(12) United States Patent
Zhang et al.

(10) Patent No.: US 9,549,706 B2
(45) Date of Patent: Jan. 24, 2017

(54) CRADLE DRIVE MECHANISM, A TABLE, AND A PATIENT IMAGING AND CARRYING APPARATUS

(71) Applicant: GE Medical Systems Global Technology Company, LLC, Waukesha, WI (US)

(72) Inventors: Xiaoyan Zhang, Beijing (CN); Xuyong Yang, Beijing (CN); Yanguo Yang, Beijing (CN); Feng Yang, Beijing (CN); Jia Liu, Beijing (CN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/161,821

(22) Filed: Jan. 23, 2014

(65) Prior Publication Data

US 2014/0208509 A1   Jul. 31, 2014

(30) Foreign Application Priority Data

Jan. 31, 2013   (CN) .......................... 2013 1 0038024

(51) Int. Cl.
| | |
|---|---|
| *A61B 6/04* | (2006.01) |
| *A61B 5/055* | (2006.01) |
| *A61B 6/00* | (2006.01) |
| *A61B 5/00* | (2006.01) |

(52) U.S. Cl.
CPC ........... *A61B 6/0407* (2013.01); *A61B 5/0555* (2013.01); *A61B 6/0428* (2013.01); *A61B 6/0471* (2013.01); *A61B 5/0035* (2013.01); *A61B 6/4417* (2013.01)

(58) Field of Classification Search
CPC ... A61B 6/0407; A61B 6/0471; A61B 6/0428; A61B 5/0555; A61B 6/4417
USPC ............. 5/601, 81.1 C; 378/209; 384/57, 58, 384/256–258; 492/27; 198/322
See application file for complete search history.

(56) References Cited

U.S. PATENT DOCUMENTS

| | | | | |
|---|---|---|---|---|
| 2,049,555 | A | * | 8/1936 | Zaparka ........................... 267/30 |
| 3,748,698 | A | * | 7/1973 | Lachmann ......................... 24/38 |
| 3,810,263 | A | * | 5/1974 | Taylor et al. ................. 5/81.1 C |
| 4,826,128 | A | * | 5/1989 | Schmeller ...................... 248/669 |
| 4,836,520 | A | * | 6/1989 | Span ................................. 5/601 |
| 5,024,312 | A | * | 6/1991 | Godbersen ...................... 193/37 |
| 5,210,893 | A | * | 5/1993 | Uosaki et al. .................... 5/601 |
| 5,316,329 | A | * | 5/1994 | MacKarvich .............. 280/414.1 |
| 5,337,875 | A | * | 8/1994 | Lee ............................. 193/35 R |

(Continued)

*Primary Examiner* — Nicholas Polito
*Assistant Examiner* — Myles Throop

(57) ABSTRACT

A cradle drive mechanism, a table and a patient imaging and carrying apparatus are provided. The cradle drive mechanism includes: a first portion, which is arranged on a main base and has a belt drive structure, wherein the belt drive structure is used to connect a cradle and drive the cradle to make a reciprocating motion; a second portion, which is arranged on a secondary base and has a secondary supporting and rotating member, wherein the second portion and the first portion form a gap therebetween, and the secondary supporting and rotating member is used to support the cradle; and two guiding and rotating members, which are arranged on the second portion and/or the first portion for guiding the cradle to move linearly. The present application can simplify the structure by adoption of the belt drive structure. Further, the gap between the second portion and the first portion does not attenuate the X-ray additionally, so the dose of the X-ray emitted can be decreased.

17 Claims, 10 Drawing Sheets

(56) References Cited

U.S. PATENT DOCUMENTS

| | | | |
|---|---|---|---|
| 5,490,296 A * | 2/1996 | Fleury et al. | 5/601 |
| 5,619,763 A * | 4/1997 | Randolph et al. | 5/601 |
| 6,185,272 B1 | 2/2001 | Hiraoglu et al. | |
| 6,640,363 B1 * | 11/2003 | Pattee et al. | 5/601 |
| 6,782,571 B1 | 8/2004 | Josephson et al. | |
| 7,072,434 B1 | 7/2006 | Tybinkowski et al. | |
| 7,370,747 B2 * | 5/2008 | Ruiz | 193/35 R |
| 7,373,676 B2 * | 5/2008 | Markovic et al. | 5/601 |
| 7,762,387 B2 * | 7/2010 | Dunn | 198/823 |
| 7,874,030 B2 * | 1/2011 | Cho et al. | 5/601 |
| 2012/0000016 A1 * | 1/2012 | Dong et al. | 5/601 |

\* cited by examiner

CRADLE DRIVE MECHANISM, A TABLE, AND A PATIENT IMAGING AND CARRYING APPARATUS

TECHNICAL FIELD

The present application relates to the field of medical imaging apparatus, and more particularly, to a cradle drive mechanism, a table having such cradle drive mechanism, and a patient imaging and carrying apparatus having such table.

BACKGROUND TECHNOLOGY

Generally, a patient can be scanned and imaged by a variety of imaging techniques in order to make diagnosis. Such imaging techniques can include X-ray imaging, magnetic resonance imaging (MRI), computer tomography (CT), positron emission tomography (PET) and the like. A patient imaging and carrying apparatus employing such imaging techniques generally includes a movable table so as to carry and position the patient accurately.

As shown in FIG. 1, a patient imaging and carrying apparatus includes the following three portions: a table 21, an imaging system 22 and a rear pedestal 23. In this apparatus, the imaging system 22 is an X-ray imaging system. The table 21 is movable, in order to get close to the imaging system 22. The table 21 can also move up and down so that the vertical position of the patient can be adjusted. The table 21 includes a cradle 24, and the cradle 24 can move relative to the table 21 in order to carry the patient into the space of the imaging system 22. When the front part of the cradle 24 passes through the imaging system 22 and moves out of the imaging system 22, a bridge 25 within the imaging system 22 can support the cradle 24. The rear pedestal 23 includes a cradle traction element 26 and a drive motor 27 thereon. The drive motor 27 can drive the cradle traction element 26. The cradle traction element 26 can pass through and protrude out of the imaging system 22 to couple with the cradle 24, thereby to drive the cradle 24 to move.

The structure of such apparatus has the following problems. Firstly, the existence of the rear pedestal 23 causes a complex structure and requires a rather larger room, such that this apparatus has high cost and the physician is not convenient to operate on the patient while performing imaging for diagnosis due to the rear pedestal 23. Secondly, because the cradle 24 needs to be supported by the bridge 25 and the bridge 25 may attenuate a portion of the X-ray, a dose of the X-ray emitted should be increased to assure a normal imaging. However, this increased dose of the X-ray is detrimental to the patient.

Further, the above cradle 24 generally slides relative to the table 21. For example, referring to FIG. 2, a cradle utilizing the sliding movement is shown, and which is described in U.S. Pat. No. 6,782,571. The cradle 820 shown in FIG. 2 can be used in the X-ray imaging system, and is an elongated member with a wide end 822, a middle 824 and a narrow end 826. The cradle 820 includes rails 840 which are configured to be received by guide rails. The rails 840 are only located at the wide end 822 of the cradle 820, such that the cradle 820 is a cantilever structure.

However, this sliding structure also has the following problems. Firstly, the cantilever structure is complex, and can increase the cost of the whole imaging system. Secondly, the cradle 820 with the cantilever structure tends to sag at a location lacking support when the patient is carried on the cradle 820. A large deformation of the cradle 820 will cause inaccurate locating for the part of the patient to be imaged.

Therefore, there is a need for a cradle drive mechanism, a table and a patient imaging and carrying apparatus that can overcome the above mentioned disadvantages.

SUMMARY OF INVENTION

In order to solve the technical problem of complex drive mechanism of the cradle of prior art, the present application provides a cradle drive mechanism.

In one aspect, the present cradle drive mechanism includes: a first portion, which is arranged on a main base and has a belt drive structure, wherein the belt drive structure is used to connect a cradle and drive the cradle to make a reciprocating motion; a second portion, which is arranged on a secondary base and has a secondary supporting and rotating member, wherein the second portion and the first portion form a gap therebetween, and the secondary supporting and rotating member is used to support the cradle; and two guiding and rotating members, which are arranged on the second portion and/or the first portion for guiding the cradle to move linearly.

According to a first preferred aspect of the present application, the first portion further includes a main supporting and rotating member, and the main supporting and rotating member and the secondary supporting and rotating member are arranged in the same plane so as to support the cradle when the cradle passes thereon.

According to a second preferred aspect of the present application (which is based on the above first preferred aspect), the first portion has one said main supporting and rotating member at one end adjacent to the gap, and the second portion has one said the secondary supporting and rotating member at one end adjacent to the gap.

According to a third preferred aspect of the present application, the belt drive structure includes a drive motor, a drive belt, an active rotating member and a passive rotating member, the drive belt is set around the active rotating member and the passive rotating member, and the drive motor drives the active rotating member to rotate for driving the drive belt to move.

According to a fourth preferred aspect of the present application (which is based on the above third preferred aspect), the belt drive structure further includes a middle supporting and rotating member, and the middle supporting and rotating member is arranged between the active rotating member and the passive rotating member so as to support the drive belt and the cradle.

According to a fifth preferred aspect of the present application, the first portion further includes a main frame, the belt drive structure is arranged on the main frame, and the guiding and rotating member is also arranged on the main frame when the guiding and rotating member is arranged on the first portion.

According to a sixth preferred aspect of the present application, the second portion further includes a secondary frame, the secondary supporting and rotating member is arranged on the secondary frame, and the guiding and rotating member is also arranged on the secondary frame when the guiding and rotating member is arranged on the second portion.

According to a seventh preferred aspect of the present application, the two guiding and rotating members are arranged adjacent to the gap, and the two guiding and rotating members are configured to respectively contact with two side portions of the bottom face of the cradle, wherein the two side portions of the bottom face of the cradle are inclined upwards and outwards, and each guiding and rotating member is arranged to be inclined upwards and outwards.

According to an eighth preferred aspect (which is based on the above seventh preferred aspect), each guiding and rotating member includes a roller, bearings, an inclined shaft and a support block, the roller is mounted on the inclined shaft via the bearings for rotating about the inclined shaft, and the inclined shaft is mounted on the support block so as to make the guiding and rotating member be inclined upwards and outwards.

According to a ninth preferred aspect (which is based on the above eighth preferred aspect), each guiding and rotating member further includes an adjusting bolt, the adjusting bolt is arranged in the support block and can adjust an inclination angle of the inclined shaft by rotation thereof.

According to a tenth preferred aspect (which is based on the above ninth preferred aspect), each guiding and rotating member further includes an elastic body and a washer, the elastic body and the washer are arranged between the adjusting bolt and one end of the inclined shaft such that the elastic body contacts with said one end of the inclined shaft, and the washer contacts with the adjusting bolt, and the elastic body is supported by the washer.

According to an eleventh preferred aspect (which is based on the above third preferred aspect), two ends of the drive belt are connected via one connection part, and the connection part is further connected to an end of the cradle away from the second portion.

According to a twelfth preferred aspect (which is based on the above third preferred aspect), two ends of the drive belt are connected via a first connection part, and the first connection part is further connected to a second connection part which is arranged on an end of the cradle away from the second portion.

According to a thirteenth preferred aspect (which is based on the above third preferred aspect), two ends of the drive belt are connected via one connection part, and the cradle is connected to the drive belt at a location away from the second portion.

According to a fourteenth preferred aspect of the present application, the cradle drive mechanism further includes more guiding and rotating members, wherein all these guiding and rotating members are distributed at two sides of the gap.

According to a fifteenth preferred aspect (which may be further based on the fourteenth preferred aspect), each two guiding and rotating members are arranged in alignment or in misalignment.

According to a sixteenth preferred aspect (which is based on the above first preferred aspect), the main supporting and rotating member and the secondary supporting and rotating member are arranged at even spacing.

According to a seventeenth preferred aspect (which is based on the above fourth preferred aspect), the first portion further includes a main supporting and rotating member, and the main supporting and rotating member and the secondary supporting and rotating member are arranged in the same plane so as to support the cradle when the cradle passes thereon, and the main supporting and rotating member the middle supporting and rotating member and the secondary supporting and rotating member are arranged at even spacing.

The present application further provides a table. The table includes a cradle and any one of the above mentioned the cradle drive mechanism. The cradle is connected to the belt drive structure so as to be driven by the belt drive structure for reciprocating motion, the secondary supporting and rotating member is configured to support the cradle, and the guiding and rotating members are configured to guide the cradle to move linearly.

Preferably, a bottom face of the cradle includes a middle portion along the longitudinal axis thereof and two side portions at two sides of the middle portion, each of the two side portions is inclined upwards and outwards.

The present application further provides a patient imaging and carrying apparatus which includes an imaging system and one of the above mentioned tables. The cradle can enter into space of the imaging system by the driving of the belt drive structure.

Preferably, the imaging system is an X-ray imaging system, a magnetic resonance imaging system, a nuclear medicine imaging system, an X-ray and nuclear medicine combined imaging system, or a radiotherapeutic apparatus.

Compare to the prior art, the cradle drive mechanism, the table and the patient imaging and carrying apparatus of the present application can have the following benefits. The present application can simplify the structure by adoption of the belt drive structure compared to the conventional sliding movement manner. Further, the gap between the second portion and the first portion does not attenuate the X-ray additionally and the structure for supporting the cradle at two sides of the scan plane enables that the cradle with lower X-ray attenuation can be used, so the dose of the X-ray emitted can be decreased. Still further, because the main supporting and rotating member and the secondary supporting and rotating member are respectively arranged adjacent to two sides of the gap, the cradle can be supported by the main supporting and rotating member and the secondary supporting and rotating member when moving above the gap, and the sag and deformation will thereby not be occurred. Therefore, the image locating accuracy is enhanced and the image reformat artifact is reduced.

Details of one or more embodiments of the present application will be explained in the description of the attached drawings and embodiments. Other features, objects and advantages of the present application can become apparent from the description, attached drawings and claims.

BRIEF DESCRIPTION OF FIGURES

The present application will be described in more detail in conjunction with embodiments by referring to attached drawings which are not necessarily drawn to scale, wherein.

DETAILED DESCRIPTION TO INVENTION

The present application will be described in more detail in conjunction with embodiments. Those skilled in the art should understand that these embodiments are just some specific embodiments by way of examples, and are not intended to limit the present application and its scope.

Figure 1:
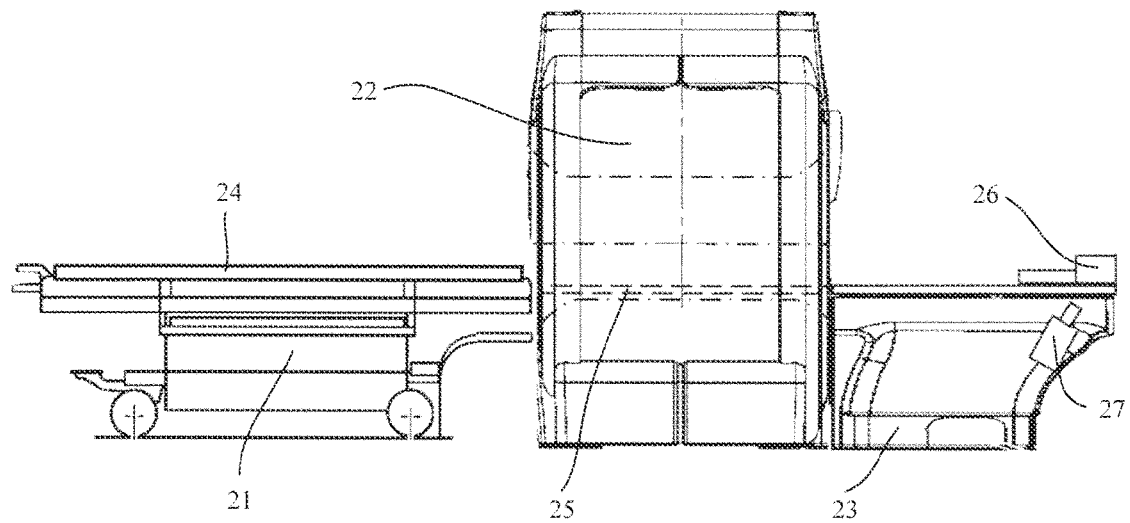
FIG. 1 is a schematic plan view illustrating a patient imaging and carrying apparatus in prior art.
Figure 2:
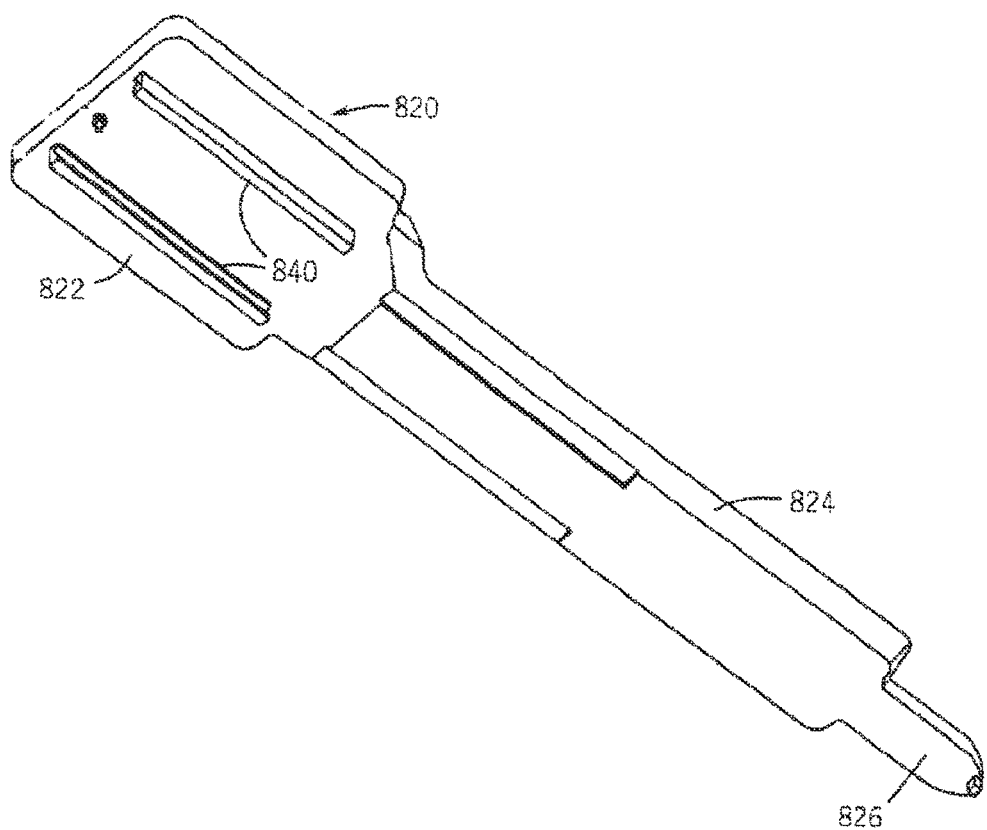
FIG. 2 is a schematic perspective view of a conventional cradle utilizing sliding movement manner.
Figure 3:
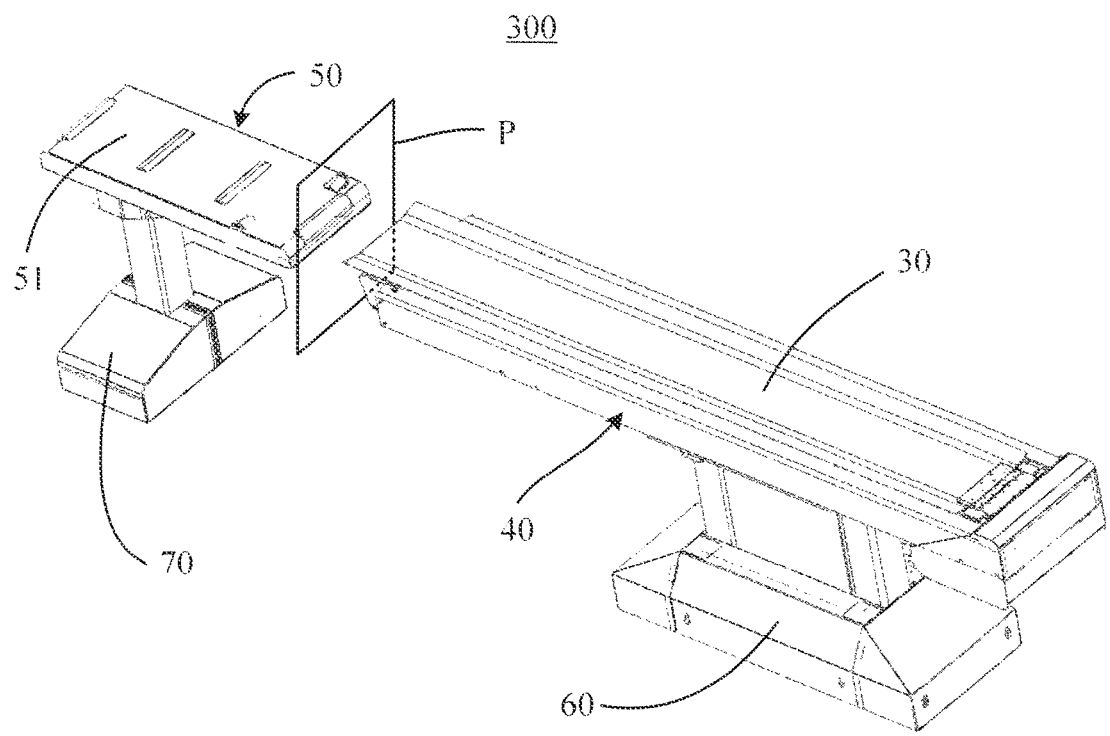
FIG. 3 is a schematic perspective view of a table according to an embodiment of the present application, which utilizes a cradle drive mechanism with belt drive manner.

Referring to FIG. 3, a schematic perspective view of a table 300 according to an embodiment is shown, which utilizes a cradle drive mechanism with belt drive manner. The table 300 includes cradle 30, a first portion (which can also be referred to as a main drive portion) 40, a second portion (which can also be referred to as a secondary drive portion or support portion) 50, a main base 60 and a secondary base 70. The first portion 40 is used for supporting the cradle 30 and a patient and driving the cradle 30 to move initially, and the second portion 50 is used for supporting the cradle 30 and the patient when the cradle 30 moves above the second portion 50. The cradle 30 can be material with lower X-ray attenuation.

Figure 4:
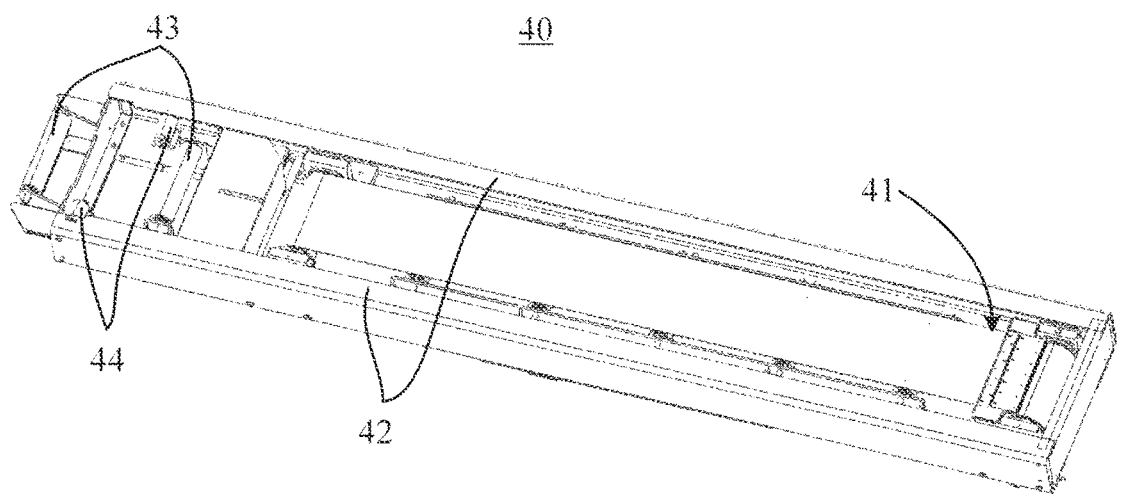
FIG. 4 is a schematic perspective view of a first portion of the cradle drive mechanism shown in FIG. 3.
Figure 5:
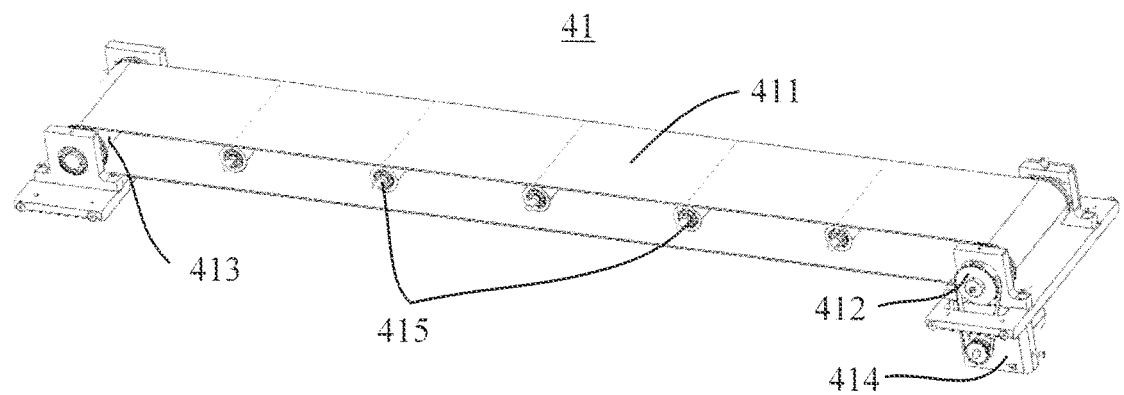
FIG. 5 is a schematic perspective view of a belt drive structure of the first portion shown in FIG. 4.

Also referring to FIG. 4 and FIG. 5, the first portion 40 is arranged on the main base 60 and has a belt drive structure 41, a main frame 42, main supporting and rotating members 43 and two guiding and rotating members 44. The belt drive structure 41 is used for connecting to the cradle 30 and driving the cradle 30 to make a reciprocating motion. The two guiding and rotating members 44 are used for guiding the cradle 30 to move linearly. The belt drive structure 41 can include a drive belt 411, an active rotating member 412, a passive rotating member 413, a drive motor 414 and middle supporting and rotating members 415. The drive belt 411 is set around the active rotating member 412 and the passive rotating member 413, and the drive motor 414 drives the active rotating member 412 to rotate for driving the drive belt 411 to move. The middle supporting and rotating members 415 can be evenly arranged between the active rotating member 412 and the passive rotating member 413 for supporting the drive belt 411 and the cradle 30. The belt drive structure 41 can be arranged on the main frame 42. The main supporting and rotating members 43 and the guiding and rotating members 44 can also be arranged on the main frame 42. The main supporting and rotating member 43 can be a main supporting roller, a main supporting wheel, and so on. The guiding and rotating member 44 can be a guiding roller, a guiding wheel, and so on. The active rotating member 412 can be an active roller, an active wheel, and so on. The passive rotating member 413 can be a passive roller, a passive wheel, and so on. The middle supporting and rotating member 415 can be a middle supporting roller, a middle supporting wheel, and so on.

Figure 6:
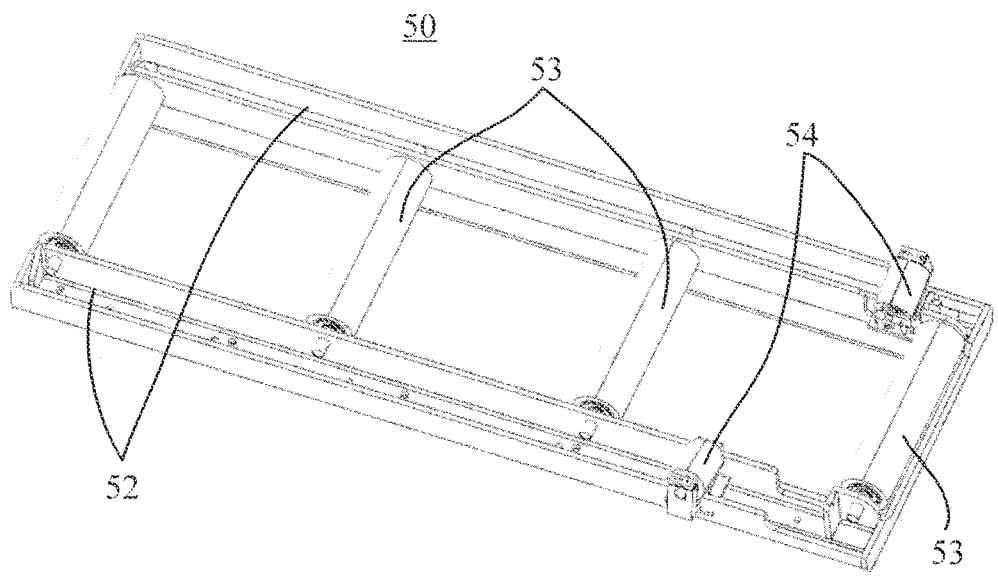
FIG. 6 is a schematic perspective view of a second portion of the cradle drive mechanism shown in FIG. 3.

Also referring to FIG. 3 and FIG. 6, the second portion 50 is arranged on the secondary base 70 and has an upper cover 51, a secondary frame 52, secondary supporting and rotating members 53 and two guiding and rotating members 54. The secondary supporting and rotating members 53 are used for supporting the cradle 30, and the two guiding and rotating members 54 are used for guiding the cradle 30 to move linearly. The secondary supporting and rotating members 53 and the guiding and rotating members 54 can be arranged on the secondary frame 52. The upper cover 51 can cover the space of the secondary frame 52. The upper cover 51 needs to have openings corresponding to the secondary supporting and rotating members 53 and the guiding and rotating members 54, so as to not prevent the secondary supporting and rotating member 53 and the guiding and rotating members 54 from contacting with a bottom face of the cradle 30. The secondary supporting and rotating member 53 can be a secondary supporting roller, a secondary supporting wheel, and so on. The guiding and rotating member 54 can be a guiding roller, a guiding wheel, and so on.

Referring to FIG. 3, the second portion 50 and the first portion 40 form a gap therebetween. The gap can be used for emission of X-ray along a scan plane P. The main supporting and rotating members 43 and the secondary supporting and rotating members 53 can be arranged in the same plane so as to support the cradle 30 when the cradle 30 passes thereon. Preferably, the first portion 40 has one main supporting and rotating member 43 (referring to FIG. 4) at one end adjacent to the gap, and the second portion 50 has one secondary supporting and rotating member 53 (referring to FIG. 6) at one end adjacent to the gap. In addition, the main supporting and rotating members 43, the middle supporting and rotating members 415 and the secondary supporting and rotating members 53 are preferably arranged at even spacing.

Figure 7:
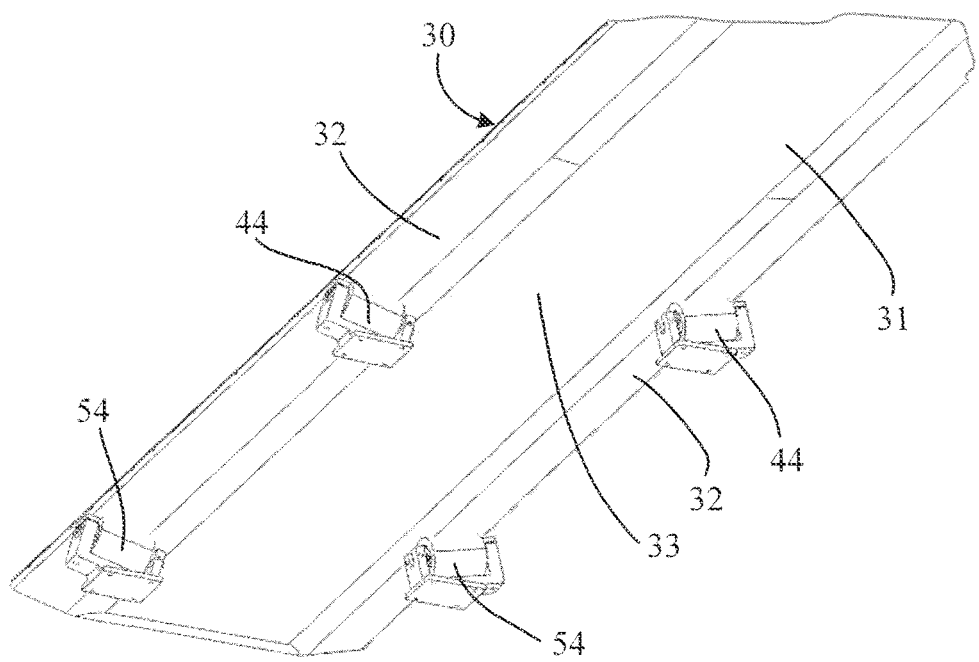
FIG. 7 is a schematic perspective view illustrating the cooperating relation between a cradle of the table shown in FIG. 3 and guiding and rotating members.
Figure 8:
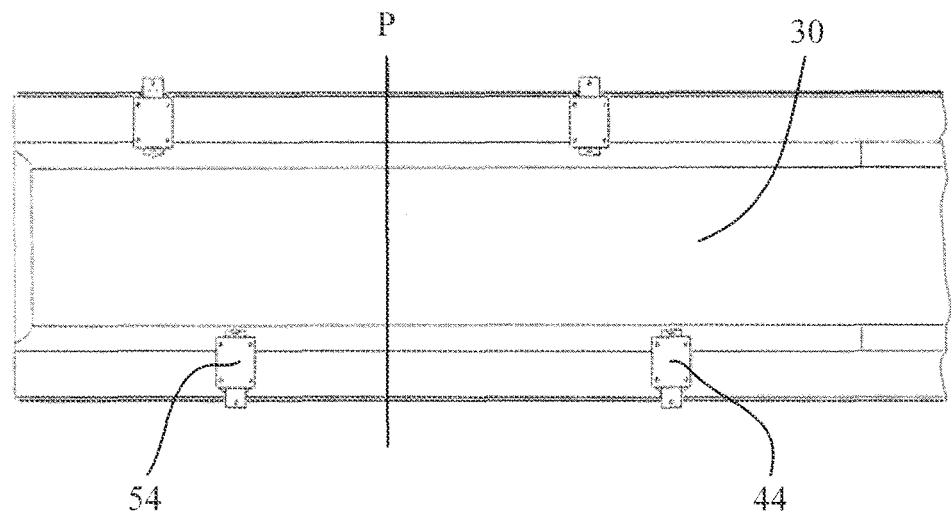
FIG. 8 is a schematic plan view of FIG. 7.

Further referring to FIG. 7 and FIG. 8, the two guiding and rotating members 44 and the two guiding and rotating members 54 can be arranged adjacent to the gap (which corresponds to the scan plane P). The bottom face 31 of the cradle 30 includes a middle portion 33 along the longitudinal axis thereof and two side portions 32 at two sides of the middle portion 33, and each of the two side portions 32 is inclined upwards and outwards. The two guiding and rotating members 44 are configured to respectively contact with the two side portions 32 of the bottom face 31 of the cradle 30, and each guiding and rotating member 44 is arranged to be inclined upwards and outwards. In other words, each guiding and rotating member 44 is arranged to be inclined upwards and outwards such that an included angle of two axes of the two guiding and rotating members 44 is less than 180 degrees. Each of the side portions 32 is inclined upwards and outwards such that an included angle of the two side portions 32 is less than 180 degrees. The arrangement manner of the two guiding and rotating members 54 can be the same with that of the two guiding and rotating members 44. It is easily understood that, only two guiding and rotating members can also achieve the guiding effect for the cradle 30 as long as the two guiding and rotating members respectively contact with the two side portions 32; here, the two guiding and rotating members can be the two guiding and rotating members 44, the two guiding and rotating members 54, or one guiding and rotating member 44 and one guiding and rotating member 54. Of course, the table 300 can further include more guiding and rotating members 44 and 54, and all these guiding and rotating members 44 and 54 can be distributed at two sides of the gap, preferably be distributed evenly. In addition, each two guiding and rotating members 44 or 54 can be arranged in alignment or in misalignment, i.e., each two guiding and rotating members 44 or 54 can be arranged along a line parallel to the scan plane P or arranged at two sides of this line.

Figure 9:
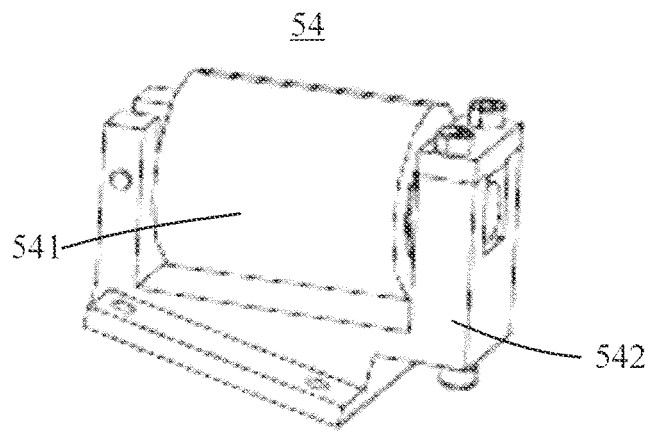
FIG. 9 is a schematic perspective view of one of the guiding and rotating members shown in FIG. 7.
Figure 10:
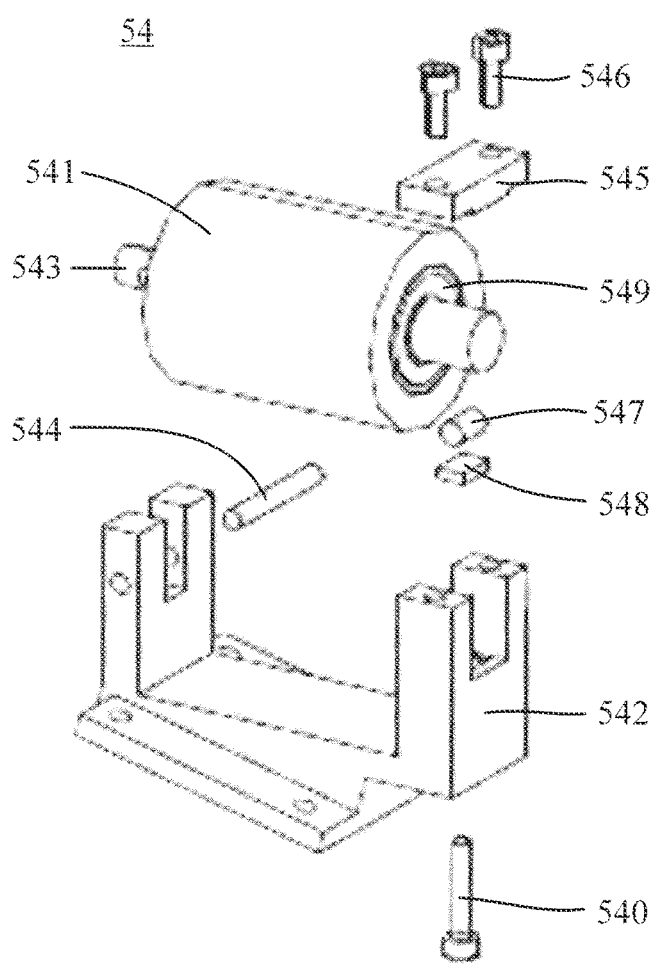
FIG. 10 is a schematic exploded view of the guiding and rotating member shown in FIG. 9.
Figure 11:
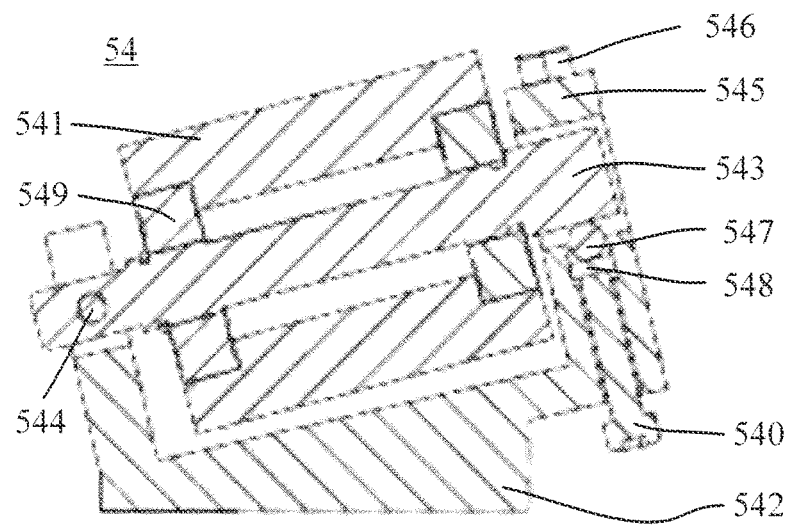
FIG. 11 is a schematic sectional view of the guiding and rotating member shown in FIG. 9, illustrating a status of the guiding and rotating member under no stress.

Referring to FIG. 9 to FIG. 11, a specific structure of the guiding and rotating members 44 and 54 is described here by referring to the guiding and rotating member 54. The guiding and rotating member 54 can include an adjusting bolt 540, a roller 541, a support block 542, an inclined shaft 543, a pin 544, a block cover 545, fastening screws 546, an elastic body 547, a washer 548 and bearings 549. The roller 541 can be mounted on the inclined shaft 543 via the bearings 549 for rotating about the inclined shaft 543. The inclined shaft 543 is mounted on the support block 542 via the pin 544 such that the inclined shaft 543 can rotate about the pin 544. The guiding and rotating members 54 are mounted on the support block 542 so as to be inclined upwards and outwards. The block cover 545 is fixed to the support block 542 via the fastening screws 546, such that one end of the inclined shaft 543 opposite to the pin 544 is received in the support block 542 and can move up and down. The adjusting bolt 540 is arranged in the support block 542 and can adjust an inclination angle of the inclined shaft 543 by rotation thereof. The elastic body 547 and the washer 548 can be arranged between the adjusting bolt 540 and said one end of the inclined shaft 543, such that the elastic body 547 contacts with said one end of the inclined shaft 543, the washer 548 contacts with the adjusting bolt 540, and the elastic body 547 is supported by the washer 548. The elastic body 547 can be an elastic rubber, a spring or other elastic structure or elastic material, and so on.

Figure 12:
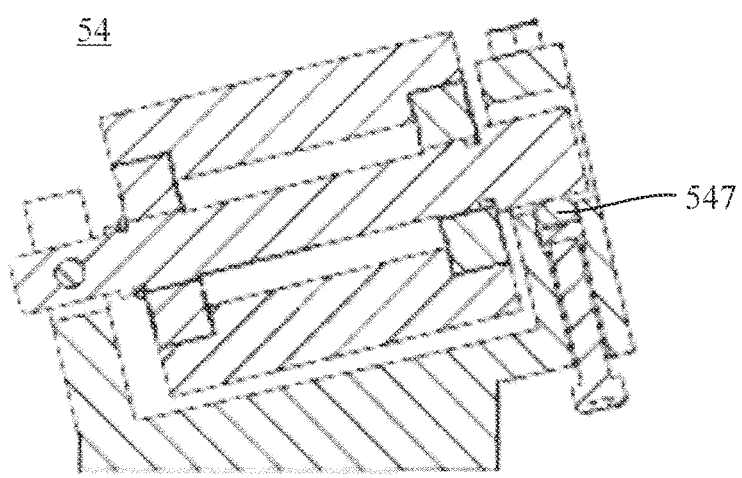
FIG. 12 is a schematic sectional view of the guiding and rotating member shown in FIG. 9, illustrating a status of the guiding and rotating member under stress.

Referring to FIG. 11, a status of the guiding and rotating member 54 under no stress is shown. Here, the elastic body 547 is under a status without deformation. Further referring to FIG. 12, a status of the guiding and rotating member 54 under stress is shown. Here, the elastic body 547 is under a status with compress and deformation. It is easily understood that, the deformation of the elastic body 547 under stress can enable the included angle of the two axes of the two guiding and rotating members 54 to adapt to the included angle of the two side portions 32 of the bottom face 31 of the cradle 30. Hereby, the cradle 30 is guided to move linearly in a favorable manner. The elastic body 547 can also cause the guiding and rotating members 54 to adapt the shape variation of the bottom face 31 of the cradle 30.

Figure 13:
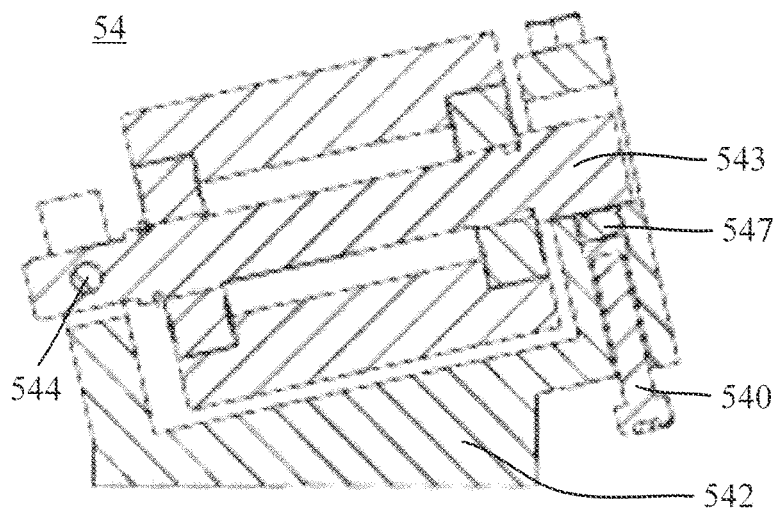
FIG. 13 is a schematic sectional view of the guiding and rotating member shown in FIG. 9, illustrating that the guiding and rotating member is at a first inclination angle.
Figure 14:
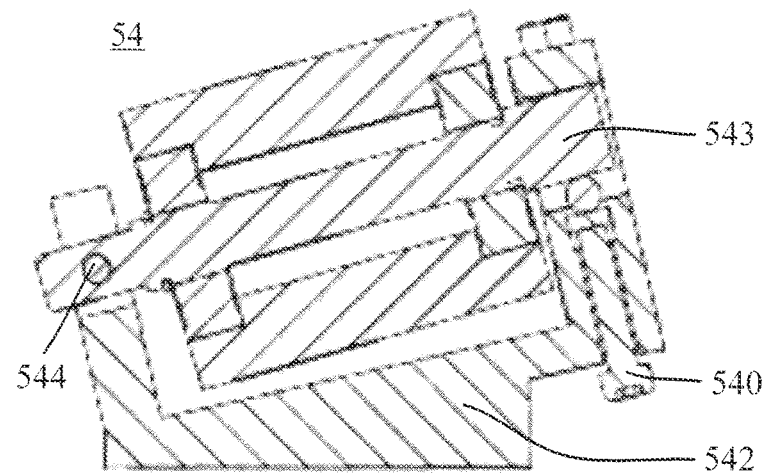
FIG. 14 is a schematic sectional view of the guiding and rotating member shown in FIG. 9, illustrating that the guiding and rotating member is at a second inclination angle.

The adjustment to the inclination angle of the inclined shaft 543 is described according to FIG. 13 and FIG. 14. Here, FIG. 13 illustrates that the adjusting bolt 540 is not completely screwed into the support block 542, such that the inclined shaft 543 is only supported by the support block 542 and the elastic body 547, and the guiding and rotating member 54 is at a first inclination angle (i.e., the minimum inclination angle). FIG. 14 illustrates that the adjusting bolt 540 is completely screwed into the support block 542, such that the end of the inclined shaft 543 is raised farthest by the adjusting bolt 540, and the guiding and rotating member 54 is at a second inclination angle (i.e., the maximum inclination angle). Of course, the inclination angle of the guiding and rotating member 54 can be adjusted as desired, such that the inclination angle is varied between the two limiting angles shown in FIG. 13 and FIG. 14. In addition, the adjusting bolt 540 can be arranged on an inner side or an outer side of the support block 542 (i.e., the left side or the right side in the figures), as long as the operation of the adjusting bolt 540 is not interfered.

Figure 15:
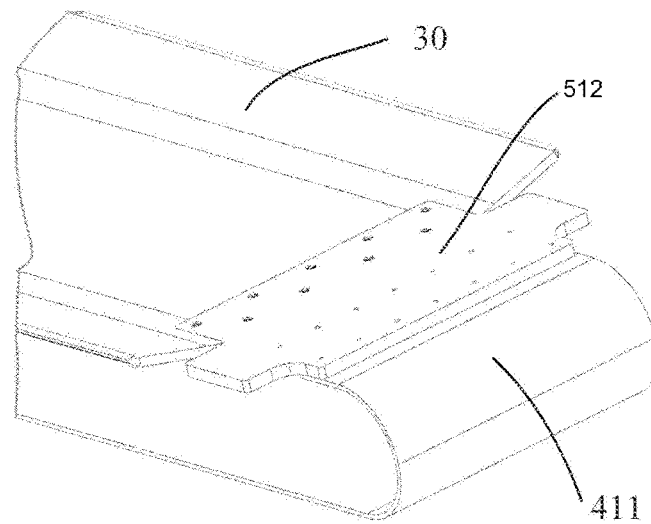
FIG. 15 is a schematic perspective view illustrating a first connection manner of a cradle of the table shown in FIG. 3 and the belt drive structure.
Figure 16:
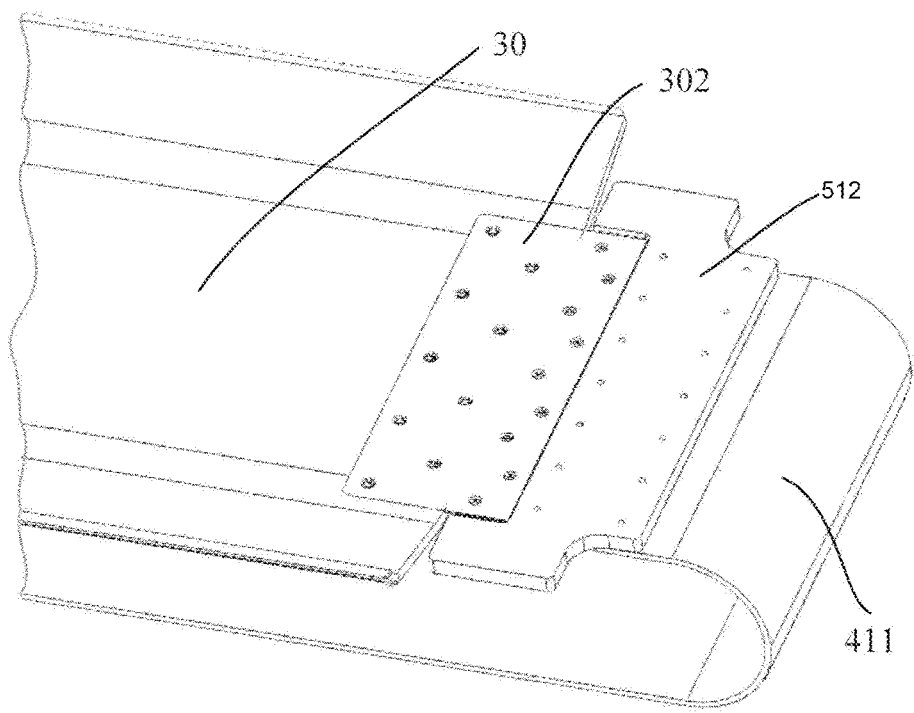
FIG. 16 is a schematic perspective view illustrating a second connection manner of the cradle of the table shown in FIG. 3 and the belt drive structure.
Figure 17:
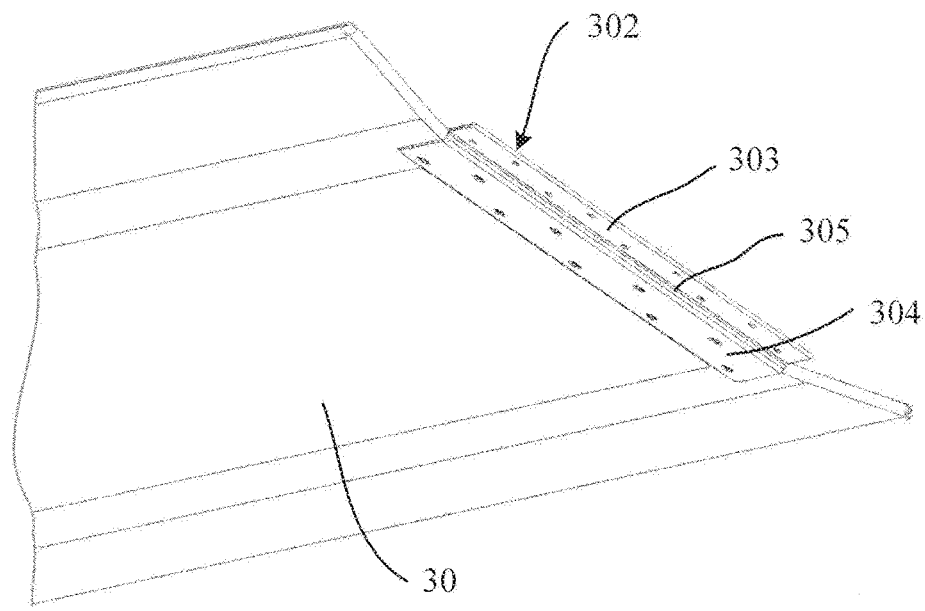
FIG. 17 is a schematic perspective view of the cradle shown in FIG. 16.
Figure 18:
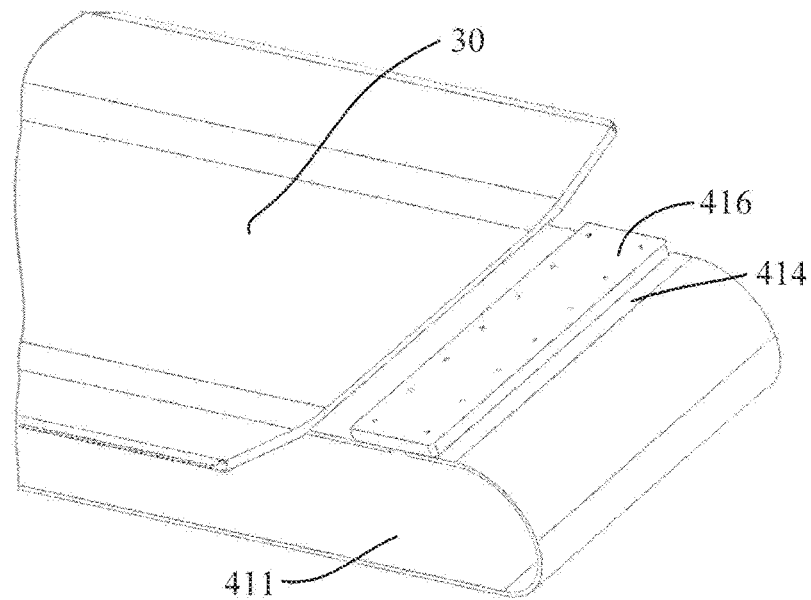
FIG. 18 is schematic perspective view illustrating a third connection manner of the cradle of the table shown in FIG. 3 and the belt drive structure.

The cradle 30 of the table 300 can be connected to the drive belt 411 in multiple manners. As shown in FIG. 15, two ends of the drive belt 411 are connected via one connection part 512 and the connection part 512 is further connected (e.g., via screws, rivets or weld, etc.) to an end of the cradle 30 away from the second portion 50. As shown in FIG. 16 and FIG. 17, two ends of the drive belt 411 are connected via a first connection part 512 and the first connection part 512 is further connected to a second connection part 302 which is arranged on an end of the cradle 30 away from the second portion 50. Here, the second connection part 302 can include two flat panels 303 and 304 which clamp the end 305 of the cradle 30 therebetween. This structure can enhance the strength of the connected location. Further referring to FIG. 18, two ends of the drive belt 411 are connected via one connection part 416, and the cradle 30 is connected to the drive belt 411 at a location away from the second portion 50 (e.g., at any location of the half segment of the cradle 30 adjacent to the connection part 416 shown in FIG. 18, as long as not precluding the drive belt 411 from driving the cradle 30 to move to its farthest distance).

The present application also discloses a patient imaging and carrying apparatus according to an embodiment. The patient imaging and carrying apparatus can adopt the table 300 shown in FIG. 3 and further includes an imaging system. Here, the cradle 30 can enter into space of the imaging system by the driving of the belt drive structure 41.

According to a preferable embodiment, the imaging system can be an X-ray imaging system. Correspondingly, the space of the imaging system is a chamber of the X-ray imaging system for receiving a part of the patient to be imaged and for irradiating using the X-ray. Of course, the imaging system can also be a computer tomography system, a magnetic resonance imaging system, a positron emission tomography system, a nuclear medicine imaging system, an X-ray and nuclear medicine combined imaging system, or a radiotherapeutic apparatus, and so on.

Compare to the prior art, the cradle drive mechanism, the table and the patient imaging and carrying apparatus of the present application can have the following benefits. The present application can simplify the structure by adoption of the belt drive structure compared to the conventional sliding movement manner. Further, in operation the gap between the second portion and the first portion does not attenuate the X-ray additionally and the structure for supporting the cradle at two sides of the scan plane enables that the cradle with lower X-ray attenuation can be used, so the dose of the X-ray emitted can be decreased. Still further, because the main supporting and rotating member and the secondary supporting and rotating member are respectively arranged adjacent to two sides of the gap (i.e., at two sides of the above mentioned scan plane), the cradle can be supported by the main supporting and rotating member and the secondary supporting and rotating member when moving above the gap, and the sag and deformation will thereby not be occurred. Therefore, the image locating accuracy is enhanced and the image reformat artifact is reduced.

The above description only illustrates the present application exemplarily, and is not intended to restrict the present application. It should be noted that for those skilled in the art, various improvements, modifications and variations can be made to the present application. However, those improvement, modifications and variations should be construed as within the protective scope of the present application without departing from the spirit of the present application.

What is claimed is:

1. A cradle drive mechanism, comprising:
a first portion comprising:
a main base,
a main supporting and rotating member; and
a belt drive structure, wherein the belt drive structure is in contact with a cradle and drives the cradle in a reciprocating motion;
a second portion comprising:
a secondary base, and
a secondary supporting and rotating member, wherein the second portion and the first portion form a gap there between, the main supporting and rotating member and the secondary supporting and rotating member being arranged in a same plane to support the cradle when the cradle passes thereon;
a guiding and rotating element comprising:
two guiding and rotating members, arranged on one of the second portion and the first portion adjacent to the gap, configured to guide the cradle, wherein the two guiding and rotating members contact corresponding side portions of a bottom face of the cradle, wherein the corresponding side portions of the bottom face of the cradle are inclined upwards and outwards, and each guiding and rotating member is configured to be inclined upwards and outwards to match corresponding side portions of the bottom face of the cradle, wherein each guiding and rotating member comprises:
a roller,
bearings,
a shaft, wherein roller is mounted on the shaft by the bearings, and
a support block, wherein the shaft is mounted on the support block to incline the roller upwards and outwards;
an adjusting bolt, the adjusting bolt arranged in the support block to adjust an inclination angle of the shaft
a washer; and
an elastic body, the elastic body being supported by the washer, wherein one end of the elastic body contacts one end of the shaft, and the washer contacts the adjusting bolt.

2. The cradle drive mechanism according to claim 1, wherein one of said main supporting and rotating member is located at one end adjacent to the gap, and one of said the secondary supporting and rotating member is located at one end adjacent to the gap.

3. The cradle drive mechanism according to claim 1, wherein the belt drive structure comprises:
a drive motor,
a drive belt,
an active rotating member, and
a passive rotating member, wherein the drive belt is set around the active rotating member and the passive rotating member, and the drive motor drives the active rotating member to rotate to move the drive belt.

4. The cradle drive mechanism according to claim 3, wherein the belt drive structure further comprises:
a middle supporting and rotating member, the middle supporting and rotating member is arranged between the active rotating member and the passive rotating member.

5. The cradle drive mechanism according to claim 1, wherein the first portion further comprises:
a main frame, wherein the belt drive structure is arranged on the main frame, and the guiding and rotating element is arranged on the main frame when the guiding and rotating member is arranged on the first portion.

6. The cradle drive mechanism according to claim 1, wherein the second portion further comprises:
a secondary frame, the secondary supporting and rotating member is arranged on the secondary frame, and the guiding and rotating element is arranged on the secondary frame when the guiding and rotating member is arranged on the second portion.

7. The cradle drive mechanism according to claim 3, wherein two ends of the drive belt are connected via one connection part, and the connection part is further connected to an end of the cradle away from the second portion.

8. The cradle drive mechanism according to claim 3, wherein two ends of the drive belt are connected via a first connection part, and the first connection part is further connected to a second connection part which is arranged on an end of the cradle away from the second portion.

9. The cradle drive mechanism according to claim 3, wherein two ends of the drive belt are connected via one connection part, and the cradle is connected to the drive belt at a location away from the second portion.

10. The cradle drive mechanism according to claim 1 further comprising:
a plurality of guiding and rotating elements, wherein the guiding and rotating elements are distributed on both sides of the gap.

11. The cradle drive mechanism according to claim 1, wherein the two guiding and rotating members are arranged opposite each other in one of: in alignment and misalignment.

12. The cradle drive mechanism according to claim 1, wherein the main supporting and rotating member and the secondary supporting and rotating member are evenly spaced.

13. The cradle drive mechanism according to claim 4, wherein the main supporting and rotating member, the middle supporting and rotating member and the secondary supporting and rotating member are arranged at even spacing.

14. A table comprising:
a cradle, and
a cradle drive mechanism comprising:
a first portion comprising:
a main base,
a main supporting and rotating member; and
a belt drive structure, wherein the belt drive structure is in contact with a cradle and drives the cradle in a reciprocating motion;
a second portion comprising:
a secondary base, and
a secondary supporting and rotating member, wherein the second portion and the first portion form a gap there between, the main supporting and rotating member and the secondary supporting and rotating member being arranged in a same plane to support the cradle when the cradle passes thereon;

a guiding and rotating element comprising:
two guiding and rotating members, arranged on one of the second portion and the first portion adjacent to the gap, configured to guide the cradle, wherein the two guiding and rotating members contact corresponding side portions of a bottom face of the cradle, wherein the corresponding side portions of the bottom face of the cradle are inclined upwards and outwards, and each guiding and rotating member is configured to be inclined upwards and outwards to match corresponding side portions of the bottom face of the cradle wherein each guiding and rotating member comprises:
a roller,
bearings,
a shaft, wherein roller is mounted on the shaft by the bearings, and
a support block, wherein the shaft is mounted on the support block to incline the roller upwards and outwards;
an adjusting bolt, the adjusting bolt arranged in the support block to adjust an inclination angle of the shaft
a washer; and
an elastic body, the elastic body being supported by the washer, wherein one end of the elastic body contacts one end of the shaft, and the washer contacts the adjusting bolt.

15. The table according to claim 14, wherein a bottom face of the cradle comprises a middle portion along a longitudinal axis thereof and two side portions at two sides of the middle portion, each of the two side portions is inclined upwards and outwards.

16. A patient imaging and carrying apparatus comprising:
an imaging system, and
a table comprising:
a cradle, and
a cradle drive mechanism comprising:
a first portion comprising:
a main base,
a main supporting and rotating member; and
a belt drive structure, wherein the belt drive structure is in contact with a cradle and drives the cradle in a reciprocating motion;
a second portion comprising:
a secondary base, and
a secondary supporting and rotating member, wherein the second portion and the first portion form a gap there between, the main supporting and rotating member and the secondary supporting and rotating member being arranged in a same plane to support the cradle when the cradle passes thereon;
a guiding and rotating element comprising:
two guiding and rotating members, arranged on one of the second portion and the first portion adjacent the gap, configured to guide the cradle, wherein the two guiding and rotating members contact corresponding side portions of a bottom face of the cradle, wherein the corresponding side portions of the bottom face of the cradle are inclined upwards and outwards, and each guiding and rotating member is configured to be inclined upwards and outward to match corresponding side portions of the bottom face of the cradle, wherein each guiding and rotating member comprises:
a roller,
bearings,
a shaft, wherein roller is mounted on the shaft by the bearings, and
a support block, wherein the shaft is mounted on the support block to incline the roller upwards and outwards;
an adjusting bolt, the adjusting bolt arranged in the support block to adjust an inclination angle of the shaft
a washer; and
an elastic body, the elastic body being supported by the washer, wherein one end of the elastic body contacts one end of the shaft, and the washer contacts the adjusting bolt and wherein the cradle can enter into a space of the imaging system by the belt drive structure.

17. The patient imaging and carrying apparatus according to claim 16, wherein the imaging system is one of: an X-ray imaging system, a magnetic resonance imaging system, a nuclear medicine imaging system, an X-ray and nuclear medicine combined imaging system, and a radiotherapeutic apparatus.

* * * * *